United States Patent [19]

Bauer

[11] 4,226,805

[45] Oct. 7, 1980

[54] SULFONATION OF OILS

[75] Inventor: Oscar W. Bauer, Petrolia, Pa.

[73] Assignee: Witco Chemical Corporation, New York, N.Y.

[21] Appl. No.: 721,903

[22] Filed: Sep. 9, 1976

Related U.S. Application Data

[63] Continuation of Ser. No. 602,616, Aug. 7, 1975, abandoned, which is a continuation-in-part of Ser. No. 400,457, Sep. 24, 1973, abandoned, which is a continuation of Ser. No. 102,946, Dec. 30, 1970, abandoned.

[51] Int. Cl.³ .......................................... C07C 143/24
[52] U.S. Cl. ............................. 260/505 R; 260/505 P
[58] Field of Search ............... 260/505 S, 505 R, 68.6, 260/458

[56] References Cited

U.S. PATENT DOCUMENTS 3,462,474  8/1969  Michener et al. ................... 260/508

*Primary Examiner*—Alan Siegel
*Attorney, Agent, or Firm*—Albert L. Gazzola; Morton Friedman

[57] ABSTRACT

Aromatic petroleum oils are diluted with a sulfonic acid to reduce agglomeration of intractable sludge during simple sulfonation with sulfur trioxide at substantially atmospheric pressure.

10 Claims, No Drawings

SULFONATION OF OILS

This application is a continuation of application Ser. No. 602,616, filed Aug. 7, 1975, which is a continuation-in-part of Ser. No. 400,457, filed Sept. 24, 1973, which is a continuation of Ser. No. 102,946, filed Dec. 30, 1970, all three now abandoned.

It has been generally recognized in the sulfonation art that sulfur trioxide in its free form theoretically provides an ideal sulfonating agent because of its highly reactive nature, and because it sulfonates organic compounds with a minimum of side reactions. However, during the sulfonation at atmospheric pressure of highly aromatic petroleum fractions with sulfur trioxide, even when diluted with nitrogen or air, agglomeration of acid sludges commonly renders the reaction mass so viscous that it becomes difficult if not impossible to stir or mix; thus sulfonation at atmospheric pressure becomes highly impractical, if not impossible.

It is known in the art that sludge buildup and reaction mass viscosity may be reduced by using a lower alkyl chlorinated solvent such as 1,2-dichloroethane (EDC) in the sulfonation of highly aromatic petroleum fractions, such as is disclosed in U.S. Pat. No. 2,783,273, issued Feb. 26, 1957 to Verley et al. The use of such solvents presents the need for an additional step of solvent recovery, however, and adds to the cost of the product. Furthermore, the hydrogen chloride by-product formed when using EDC during sulfonation results in premature corrosion of equipment. In addition EDC itself reacts with the sulfonating agent ($SO_3$), thus requiring a corresponding excess of each for maximal sulfonation.

Other prior art methods for improving sulfonation procedures, such as found in U.S. Pat. No. 2,523,582, issued Sept. 26, 1950 to Mattson; U.S. Pat. No. 2,616,936, issued Nov. 4, 1952 to Mammen et al.; U.S. Pat. No. 2,828,331, issued Mar. 25, 1958 to Marisic et al.; U.S. Pat. No. 3,024,258, issued Mar. 6, 1962 to Brooks et al.; U.S. Pat. No. 3,056,831, issued Oct. 3, 1962 to Stratford et al.; and U.S. Pat. No. 3,232,976, issued Feb. 1, 1966 to Lohr, commonly require heavy and expensive equipment with added maintenance costs, laborious manipulation, and generally leave much to be desired.

According to the present invention, I have discovered that when aromatic petroleum oils are diluted with a liquid sulfonic acid, and sulfonation at atmospheric pressure is effected with sulfur trioxide, the sulfonation proceeds at least as smoothly as when using EDC; sulfur trioxide sludge formation becomes manageable; high yields of useful sulfonic acids are produced; and the resulting acid oils may be converted to the corresponding metal sulfonates in good yield.

Sulfonic acids having an average molecular weight in the range of about 300–600 and preferably 380–520 may be used as diluents in the process of the present invention. These may be alkyl benzenoid sulfonic acids such as alkyl benzene or alkyl toluene sulfonic acids, for instance wherein the alkyl moiety contains from about 10–13 carbons and mixtures thereof. Both natural and synthetic sulfonic acids and mixtures thereof may be used. Natural sulfonic acids are obtained from sulfonation of certain solvent extracted petroleum distillates, whereas synthetic sulfonic acids are obtained by sulfonation of a commercially synthesized alkyl aromatic hydrocarbon. Illustrative examples of such sulfonic acids are decylbenzene sulfonic acid, undecylbenzene sulfonic acid, dodecylbenzene sulfonic acid, tridecylbenzene sulfonic acid, tetradecylbenzene sulfonic acid, pentadecylbenzene sulfonic acid, hexadecylbenzene sulfonic acid, octadecylbenzene sulfonic acid, eicosylbenzene sulfonic acid, and the corresponding higher alkyl derivatives of toluene sulfonic acid, ethylbenzene sulfonic acid, isopropylbenzene sulfonic acid, naphthalene sulfonic acid, methylnaphthalene sulfonic acid and isopropylnaphthalene sulfonic acid and the like and mixtures thereof. The alkyl or long chain radicals of the foregoing sulfonic acids can be straight chain or branched chain, but it is preferred that they be straight chain or predominately straight chain.

Preferred sulfonic acids for use as diluents in the present invention are those having an average molecular weight of about 440, being derived from a heavy alkylate bottom fraction having an average of about 20 carbon atoms in the alkyl moiety, such as bottoms from the synthesis of dodecyl benzene, or sulfonic acids derived from mahogany sulfonates having longer aliphatic chains. The sulfonic acid diluent may be extraneous or may be the same sulfonic acid of the aromatic petroleum fraction to be sulfonated.

The sulfonic acid diluent, according to the present invention, may be present in concentrations of as little as about 3% based on the weight of the aromatic feedstock, and as high as about 50%, or more. For instance, the concentration of sulfonic acid diluent may be as little as 3–5% with low aromatic oils and as much as 30–50% or somewhat more with highly aromatic oils. The quantity of sulfonic acid utilized is subject to practical considerations as to higher concentrations. Excellent results are achieved using a weight of sulfonic acid in the range of between 3 and 25% for sulfonating feedstocks having a viscosity of from 50 SSU to up to 3,000 SSU at 100° F.

The present process is particularly useful in the sulfonation of heavy alkyl aromatic petroleum fractions, although feedstocks ranging from heavy gas oil to light stocks may be sulfonated by the process of this invention.

The feedstock may be added to the sulfonic acid diluent in the reaction zone, preferably in toto, or it may be added incrementally while passing the sulfur trioxide through the reaction mixture. In either case, vigorous agitation is applied during the addition.

Proportions of sulfur trioxide ranging from about 5–40 weight percent based on the oil stock and preferably about 16–30 weight percent may be used in the present sulfonation process. Excess over 30 weight percent of sulfur trioxide may not lead to any appreciably higher yield and contributes to waste of the sulfur trioxide and unwanted side reactions.

It is preferred to dilute the sulfur trioxide with a dry inert gas such as nitrogen or with air, as is known in the art, to provide a better distribution of the sulfonating agent for ease of sulfonation and better yield. One part of sulfur trioxide to 9 parts of inert gas diluent renders a workable dilution for most sulfonations, but the extent of this dilution is not critical to the present invention, and only subject to practical limits. In either case, the sulfur trioxide is generally slowly added to the hot agitated reaction mixture at atmospheric pressure.

The time of reaction may vary from 1 to 3 hours or may be complete in 10–20 minutes depending on the amount of $SO_3$ required and on the reactivity and viscosity of the aromatic petroleum fraction being sulfonated.

The temperature in the reaction zone is preferred elevated and may be in the range of 110°–200° F., preferably at 140°–180° F. Very vigorous agitation of the reaction mixture during the sulfonation is preferred for best results.

After the reaction is complete, the sludge or insolubles may be separated off and the substantially sludge-free concentrate of sulfonic acid may be converted to the particular metal sulfonate desired. For example, the acid oil is reacted with a metal oxide or hydroxide to produce the respective metal petroleum sulfonate. Alternatively, the entire acidified reaction mass may be neutralized with a metal oxide or hydroxide.

The following examples illustrate specific embodiments of this invention and are not intended to define the scope of the present invention:

EXAMPLE 1

A non-solvent extracted petroleum gas oil, containing about 52% aromatics and having a viscosity of 298 SUS at 130° F., which forms a tough unmanageable sludge when sulfonation is attempted with $SO_3$, is diluted at about 25% wt/wt with an alkyl benzene sulfonic acid having an average of 18 carbons in the alkyl moiety, while stirring vigorously at a temperature of 170°–180° F. $SO_3$ gas, diluted with dry air, is added to the vigorously stirred hot reaction mixture over 2 to 3 hours. About 20–25% by weight of $SO_3$ based on the feedstock weight is added during the reaction period. The entire reaction mass is neutralized with an aqueous solution of sodium hydroxide. Sodium sulfonate is then extracted from the unreacted oil with aqueous alcohol. The sulfonate yield from the gas oil is about 50% by weight based on the original weight of the oil and the sodium sulfonate has an average molecular weight of about 410.

EXAMPLE 2

Additional gas oil is added to an acidified product prepared as in Example 1, and sulfonation with $SO_3$ is continued. The reaction mass is allowed to settle and sludge separated from the acidified top layer containing the sulfonic acids of interest. Gas oil is then again added incrementally to a portion of the acidified top layer and sulfonated to completion with $SO_3$. The above cycle may be repeated continuously. The acidified products isolated from the above continuous procedure are neutralized and treated as in Example 1.

EXAMPLE 3

A sample of dewaxed and hydrofined, highly aromatic lube oil having a viscosity of 75 SUS at 100° F. and an Index of Refraction at 25° C. of 1.4794, which forms a tough unmanageable sludge when sulfonation is attempted with $SO_3$, is added incrementally to a sulfonic acid made from the same oil stock, while adding $SO_3$ diluted with dry air. The aromatic oil is added in three increments totaling 375 g. to a previously prepared acidified 250 g. portion of the same oil, containing about 20% sulfonic acid, with vigorous agitation of the reaction mass at 150° F. About 13.9% $SO_3$ is added based upon the weight of crude feedstock, over a 2-hour period, to the hot vigorously agitated reaction mixture. The reaction mixture is allowed to settle and 563 g. of acidified oil is separated from 104.7 g. of sludge. The acidified sludge-free oil is then neutralized with aqueous sodium hydroxide solution and the sodium sulfonate is separated from unsulfonated oil by extraction with aqueous alcohol, as in Example 1.

EXAMPLE 4

About 500 g. of a viscous petroleum oil of high aromatic content, having a Saybolt Viscosity at 100° F. of 2480 SUS (Kinematic viscosity at 100° F. of 535 centistokes) and a molecular weight of about 400, which forms a tough unmanageable sludge when sulfonation is attempted with $SO_3$, is added to an equal weight of a mixture of alkyl benzene sulfonic acids having an average of 20 carbons in the alkyl moiety, at 170° F. with vigorous agitation. About 100 g. of $SO_3$ diluted with dry nitrogen is passed into the hot vigorously agitated mixture over a 2.5 hour period. The reaction mixture is allowed to settle and 850 g. of acidified oil is separated from 195 g. of sludge. The acidified oil is neutralized as in Example 1 but using $Ba(OH)_2$.

EXAMPLE 5

About 400 g. of an aromatic petroleum gas oil having a molecular weight of about 270 and a viscosity of 50 SUS at 100° F. is mixed with about 18 g. of a synthetic dodecylbenzene sulfonic acid at 140° F. with vigorous agitation. About 25 g. of $SO_3$ gas, diluted with 9 volumes of dry air, is added to the hot agitated reaction mixture over 10–15 minute period. The reaction mixture is stirred for an additional 5 minutes and allowed to settle. About 360 g. of acidified oil is separated from about 65 g. of sludge.

The yield of sulfonated products will vary from batch to batch dependent upon the aromatic content of the petroleum feedstock.

Having thus described my invention, I claim:

1. In a method for sulfonating aromatic petroleum oil feedstock with sulfur trioxide, the improvement, successful in avoiding the tough, intractable sludge which otherwise forms when sulfonating said feedstock with $SO_3$ at atmospheric pressure, which consists essentially in (i) mixing at a temperature in the range of 110°–200° F. of an aromatic petroleum feedstock with a liquid sulfonic acid diluent, said diluent being present in the concentration of about 3% to about 50%, by weight, based upon the weight of the feedstock, (ii) vigorously stirring said mixture while gradually adding, over a period of about 10 minutes to about 3 hours, an amount of sulfur trioxide sufficient to sulfonate said aromatic petroleum oil feedstock at substantially atmospheric pressure, (iii) thereafter allowing the resulting product mixture of sulfonated feedstock oil and sludge to stand whereby said sludge settles out from the sulfonated oil, and (iv) separating said substantially sludge-free sulfonated oil from said sludge.

2. The method of claim 1 wherein the petroleum oil feedstock has a viscosity in the range of 50–3000 SUS at 100° F.

3. The method of claim 1 wherein the reaction temperature is between 140° and 180° F.

4. The method of claim 1 wherein said sulfonic acid diluent is derived from a heavy alkylate bottom fraction.

5. The method of claim 1 wherein said sulfonic acid diluent is present in the reaction mixture in a concentration of about 3–25 weight percent based on the petroleum oil feedstock.

6. The method of claim 1 wherein said sulfonic acid diluent is a natural sulfonated oil.

7. The method of claim 1 wherein said sulfonic acid diluent is a synthetic sulfonated oil.

8. The method of claim 1 wherein said sulfonic acid diluent is an alkyl benzene sulfonic acid having an average of about 20 carbons in the alkyl moiety.

9. The method of claim 2 wherein the reaction is conducted at a temperature between 140° and 180° F., and wherein said sulfonic acid diluent is an alkyl benzene sulfonic acid derived from a heavy alkylate bottom fraction.

10. The method of claim 9 wherein said sulfonic acid diluent is present in the reaction mixture in a concentration of about 3–25 weight percent based on the petroleum oil feedstock.

* * * * *